United States Patent [19]
Kimura

[11] Patent Number: 5,402,792
[45] Date of Patent: Apr. 4, 1995

[54] ULTRASONIC MEDICAL APPARATUS

[75] Inventor: Tatsuo Kimura, Kyoto, Japan

[73] Assignee: Shimadzu Corporation, Kyoto, Japan

[21] Appl. No.: 213,135

[22] Filed: Mar. 15, 1994

[30] Foreign Application Priority Data

Mar. 30, 1993 [JP] Japan .................. 5-072474

[51] Int. Cl.$^6$ ............................. A61B 8/00
[52] U.S. Cl. ............................. 128/663.01
[58] Field of Search ............. 128/660.09, 661.01, 128/662.03, 663.01; 73/625, 626; 310/313 R, 313 A, 328, 335, 336

[56] References Cited

U.S. PATENT DOCUMENTS

| | | | |
|---|---|---|---|
| 3,086,195 | 4/1963 | Halliday | 73/626 |
| 4,207,901 | 6/1980 | Nigam | 128/663.01 |
| 4,691,570 | 9/1987 | Hassler | 73/626 |
| 4,762,002 | 8/1988 | Adams | 73/625 |
| 5,305,731 | 4/1994 | Buchholtz | 128/663.01 |

*Primary Examiner*—George Manuel
*Attorney, Agent, or Firm*—Heller, Ehrman, White & McAuliffe

[57] ABSTRACT

An ultrasonic medical apparatus, particularly convenient for use inside a body cavity, includes an applicator having an ultrasonic transducer, which may be attached to an acoustic lens such that the emitted ultrasonic waves are focused at two or more different positions. For this purpose, the wave-emitting surface of the transducer, or the acoustic lens attached to it, is partitioned into concave surface elements which may be in a concentric annular arrangement and may each have a different radius of curvature and a different center of concavity. An apparatus thus structured can be made compact and hence is convenient for use inside a body cavity.

12 Claims, 2 Drawing Sheets

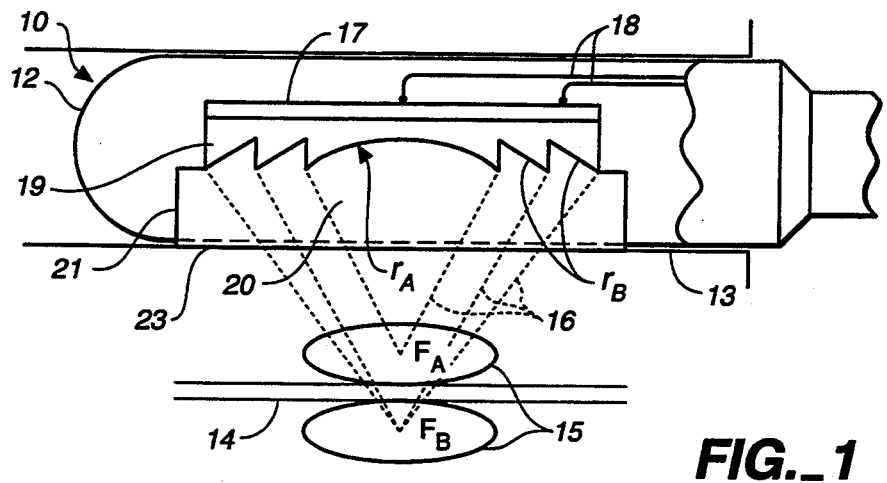
FIG._1
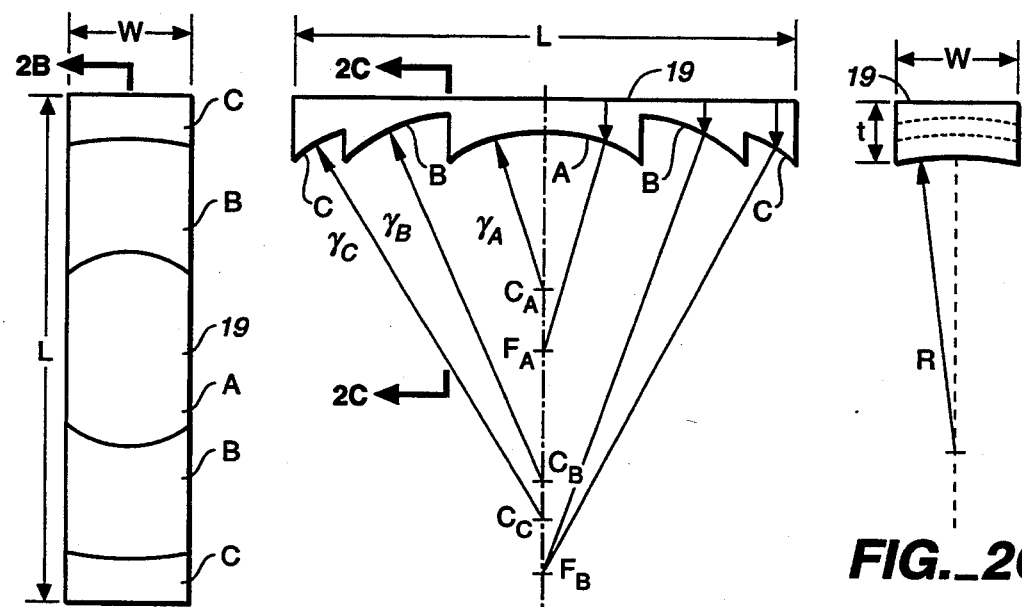
FIG._2A  FIG._2B  FIG._2C

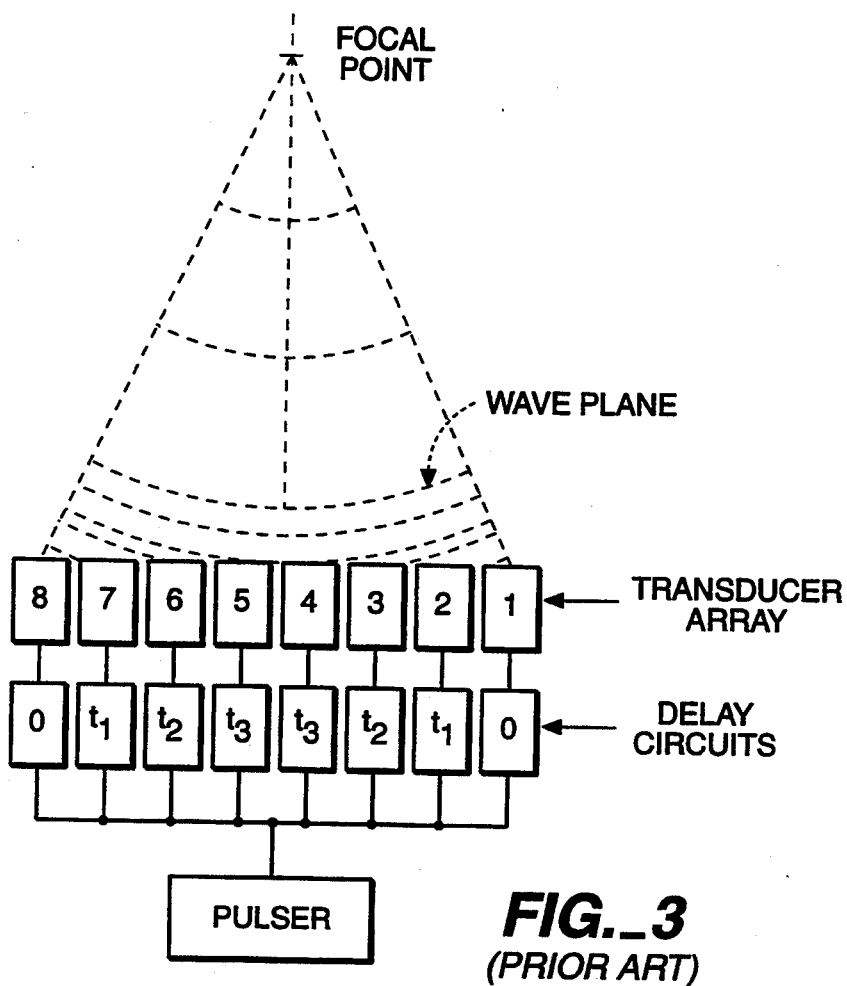
FIG._3
(PRIOR ART)
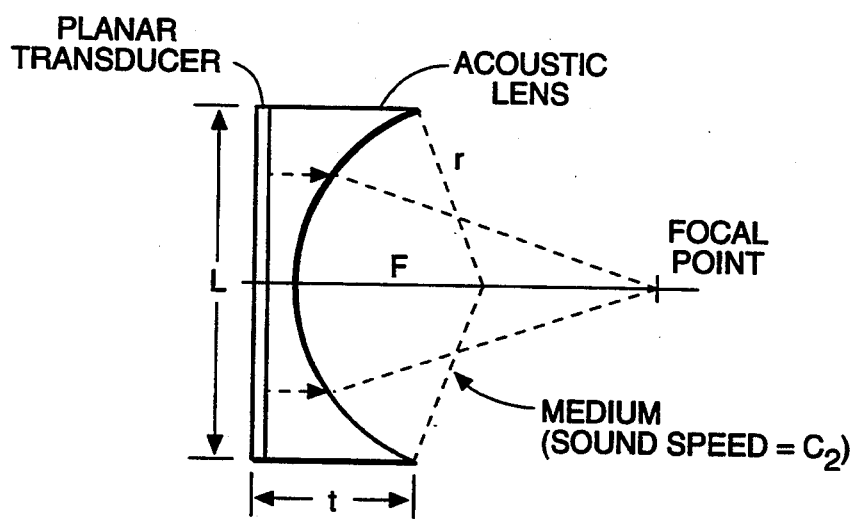
FIG._4
(PRIOR ART)

ULTRASONIC MEDICAL APPARATUS

BACKGROUND OF THE INVENTION

This invention relates to an ultrasonic medical apparatus for applying ultrasonic energy, whether generated inside or outside a patient's body, to a target area for medical treatment within the body by heating or destroying. In particular, the invention relates to an ultrasonic applicator provided with an ultrasonic transducer for such an apparatus.

In medical apparatus of this kind, it has been known to make use of an array of many planar transducers as shown in FIG. 3 so as to provide a suitable ultrasonic wave distribution within the body and to thereby electronically focus these waves at the target position, that is, by using delay circuits to control the phases of high-frequency power from a pulser (or an oscillator) for the individual transducers. Another known method for the same purpose has been to provide an acoustic lens to a planar ultrasonic transducer as shown in FIG. 4.

According to the prior art technology shown in FIG. 4, the planar transducer and the acoustic lens are in close contract with each other, and they are usually circular or quadrangular. For use inside a body cavity, in particular, a thin, elongated rectangular shape is usually adopted, and the acoustic lens is usually so shaped as to have a long concave surface with curvature in the longitudinal direction such that ultrasonic energy can be effectively focused. In other words, the diameter L of the lens must be quite large. The acoustic lens is usually made of aluminum, acryl or polystyrene. Since the speed of sound in such materials is greater than inside water, ultrasonic waves can be focused by a lens with such a concave surface.

The method of focusing ultrasonic energy shown in FIG. 3 is disadvantageous in that a very complicated electronic circuit is required for the necessary phase control and this affects the cost of the apparatus. Since as many lead lines are required as there are transducers in the array, furthermore, the diameter of the applicator also increases accordingly and the possibility of wire breakage also increases. The focusing method by an acoustic lens as shown in FIG. 4 is advantageous because the electronic circuit can be simplified and the number of components to be assembled is reduced, thereby also lowering the cost of manufacture. On the other hand, however, this method imposes a severe restriction on the shape when it is applied to an ultrasonic applicator for use inside a body cavity. For example, an applicator for use inside body cavities must be about 20-25mm in diameter. Let us assume that the diameter L of the acoustic lens of Fig, 4 is 60mm and that the lens is made of aluminum, the speed of sound therethrough being 6400m/sec. The radius of curvature r of the acoustic lens and the distance F of its focus therefrom are related as follows: $r=F(1-c_2/c_1)$, where $c_1$ is the speed of sound inside the acoustic lens and $c_2$ is the speed of sound inside the medium into which the sound is emitted from the lens. In a situation where this applicator is thrust through the anus to treat the hypertrophy of the prostate gland (or benign prostatic hyperplasia "BPH") by transrectally heating, for example, ultrasonic energy must be focused about 40mm in front of the ultra sound-radiating surface of the acoustic lens, and r becomes approximately 30.6 mm according to the formula given above if the medium is assumed to be water such that the speed of sound therein is 1500 m/sec. This means that the thickness (shown by letter t in FIG. 4) of the lens at its edges becomes very large. If an elongated cylindrical ultrasonic wave applicator for use inside body cavities is designed with a lens of this size, the applicator will be too thick to be inserted into a human body cavity such as the rectum. In other words, there is a severe dimensional limitation on transducers and acoustic lenses having a curvature (or focal length) suitable for an ultrasonic wave applicator for use inside body cavities.

One may think of reducing the diameter L of the acoustic lens such that the thickness t can be reduced, but this will also reduce the surface area of the transducer. Since there is a limit to the power output per area of the transducer, the total area of the energy-emitting surface cannot be reduced too much because it is necessary to obtain sufficient ultrasonic energy for a medical treatment must. In other words, there is a limit to how small the diameter L can be made.

It is also to be noted that, since-the target region for medical treatment usually extends in the radial direction of the emitted ultrasonic waves, it will be advantageous if the ultrasonic waves can be focused simultaneously at more than one target position because the effective region of treatment is thereby increased and the effect of treatment improves. Moreover, the time required for treatment can be shortened and, since the applicator does not have to be moved inside the body cavity in order to change its focal point, the pain to the patient can be alleviated.

SUMMARY OF THE INVENTION

In view of the above, it is an object of the invention to provide an ultrasonic applicator capable of focusing the ultrasonic waves emitted from an ultrasonic transducer at a plurality of focal points and of reducing the thickness of the ultrasonic transducer and/or an acoustic lens to be used therewith.

An ultrasonic applicator according to the present invention, with which the above and other objects can be accomplished, may be characterized as having an ultrasonic transducer or an acoustic lens, of which the ultrasonic wave-emitting surface is partitioned into a plurality of concentric concave surface elements each having a different radius of curvature as well as a different center of its concavity (or curvature). When high-frequency electric power is applied to an ultrasonic transducer and ultrasonic waves are emitted therefrom, they are generally focused at a focal point determined by the curvature of the transducer or the acoustic lens which may be provided. According to the present invention, however, the ultrasonic wave-emitting surface of the transducer and/or the lens which may be provided are divided into a plurality of surface elements having different curvatures and different centers of concavity (or curvature). Thus, the ultrasonic waves generated by the transducer are focused at a plurality of different focal points each determined by the curvature of one of these surface elements. Since the concave surfaces of the different surface elements have different centers of concavity (or curvature), furthermore, the wave-emitting surface can be made flatter as a whole and hence the total thickness of the applicator can be reduced. The number of focal points and their position can be freely determined by varying the curvatures of the individual surface elements and the centers of their concavity (or curvature).

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a structural diagram of an ultrasonic medical apparatus according to the present invention;

FIG. 2A is a plan view of the acoustic lens of FIG. 1, FIG. 2B is its sectional view taken along the line 2B—2B shown in FIG. 1A, and FIG. 2C is its sectional view taken along the line 2C—2C shown in FIG. 2B;

FIG. 3 is a schematic structural diagram of a prior art ultrasonic applicator using delay circuits; and FIG. 4 is a schematic structural diagram of another prior art ultrasonic applicator using an acoustic lens.

DETAILED DESCRIPTION OF THE INVENTION

FIG. 1 shows an ultrasonic applicator 10 for use inside a body cavity according to the invention, as having been inserted into a human rectum 11 for medical treatment and irradiating through the rectum wall 13 hypertrophied parts 15 of prostate compressing the urethra 14 from outside. The applicator 10 includes an elongated rectangular planar transducer 17 (with length L and width W), to which high-frequency electric power is adapted to be supplied from a high-frequency power source or a pulser (not shown) through lead lines 18. An acoustic lens 19 according to the present invention is attached to this planar transducer 17 by means of an adhesive such as epoxy resin such that ultrasonic waves 16 emitted from the lens 19 are propagated into the body through deaerated water 20 serving as a matching medium with the body. The deaerated water 20 is held inside a container 21 made of a thin film of silicone rubber or the like so as not to leak out of the applicator 10 into the rectum 11.

The planar transducer 17, the lead lines 18, the acoustic lens 19 and the thin-film container 21 are all contained inside a hollow cylindrical vessel 22 with a bottom piece and an opening 23 through which the thin-film container 21 protrudes outwardly, being thus exposed to the exterior.

Examples of suitable material for the acoustic lens 19 include aluminum, polymethyl methacrylate and polystyrene. Use may also be made of a composite of these materials. The lens 19 is designed to have two focal points $F_A$ and $F_B$ such that the hypertrophy 15 on both sides of the urethra 14 can be treated efficiently at the same time.

As shown more clearly in FIG. 2A, the acoustic lens 19 is of the same rectangular shape as the transducer 17 with length L and width W. A central wave-emitting concave surface element A, circular in shape to the extent that it fits inside this rectangular shape of the lens 19 as shown in FIG. 2A, is formed at its center, having a radius of curvature $r_A$ and a center of concavity (or curvature) at $C_A$ such that the ultrasonic waves from the transducer 17 passing through this central surface element A will be focused at the first focal point $F_A$. Two outer wave-emitting concave surface elements B and C are concentrically formed around and outside of the central surface element A in annular forms (again to the extent that they fit inside the rectangular shape of the lens 19 as shown in FIG. 2A), respectively having a radius of curvature $r_B$ and $r_C$ ($=r_B$) and a center of concavity at $C_B$ and $C_c$ ($\neq C_B$) as shown in FIG. 2B such that the ultrasonic waves from the transducer 17 passing through these outer surface elements B and C will be both focused at the other focal point $F_c$.

Since $C_B$ and $C_c$ are at different positions, the lens surface is jagged, the neighboring surface elements not connecting smoothly to each other. The waves emitted through the surface element A are focused at $F_A$ and those emitted through the surface elements B and C are focused at $F_B$. In other words, the radii of curvature and the focal distances satisfy the lens formula give above individually for each surface element.

Because $C_B$ and $C_c$ are at different positions although the radii of curvature $r_B$ and $r_c$ are equal to each other, the acoustic lens 19 becomes flatter as a whole. In other words, the acoustic lens 19 can be made thinner, and the applicator 10 can accordingly be made thin enough to be insertable into a body cavity.

Although the focusing of the ultrasonic waves has been described above only with reference to FIG. 2B and in the longitudinal direction of the elongated transducer 17 and the acoustic lens 19, the lens surfaces A, B and C may be made concave (with a suitable radius of curvature R) also in the transverse direction, that is, in the direction of the width W, as shown in FIG. 2C such that the waves can be focused also in this direction and a higher concentration of ultrasonic energy can be obtained. It is to be noted that the ultrasonic wave energy can be concentrated at any positions because the focal points $F_A$ and $F_B$ can be easily adjusted by changing the radii of curvature.

Although the invention has been described above with reference to only embodiment, this embodiment is not intended to limit the scope of the invention. Many modifications and variations are possible within the scope of the invention. For example, although a mutually attached combination of a planar transducer 17 and an acoustic lens 19 with concave surface elements having different curvatures and centers of concavity has been described above such that the waves passing therethrough are focused at two separate focal points $F_A$ and $F_B$, use of such an acoustic lens can be dispensed with if the ultrasonic transducer 17 is modified so as to have a shape as shown in FIGS. 2A, 2B and 2C with its wave-emitting surface partitioned into a plurality of concave surface elements having different radii of curvature and centers of concavity. Such a modified ultrasonic transducer is deemed to be shown also by FIGS. 2A, 2B and 2C, and hence is not shown separately.

Although the invention has been illustrated above as applied to an applicator for use inside a body cavity, it goes without saying that the invention can be applied to the type of applicators adapted to have ultrasonic waves generated outside the patient's body.

It also goes without saying that the number of separate focal points need not be two. It can be three or greater. Moreover, some or all of the focal points may be located off the central axis of the radiated waves.

In summary, the present invention makes it possible to cause ultrasonic waves from a transducer to become focused at a plurality of positions such that an extended treatment region or a plurality of target regions can be irradiated. This is particularly useful for the thermal treatment of a hypertrophy of prostate. Moreover, since the present invention makes it possible to reduce the size of an ultrasonic applicator, it is particularly useful for an apparatus for use inside a body cavity. Since an applicator according to the present invention does not have to be moved in order to focus the waves at different positions, the time of medical treatment can be shortened and the pain to the patient can be alleviated.

What is claimed is:

1. In an ultrasonic medical apparatus comprising an ultrasonic transducer having a wave-emitting surface, said transducer being adapted to have high-frequency electric power applied thereon, to thereby emit ultrasonic waves through said wave-emitting surface, and to focus said waves at a target position for a medical treatment, the improvement wherein said wave-emitting surface of said transducer is partitioned into a plurality of concave surface elements having different radii of curvature and different centers of concavity.

2. The apparatus of claim 1 wherein said surface elements are arranged such that said ultrasonic waves emitted through said wave-emitted surface are focused at a plurality of specified positions.

3. The apparatus of claim 2 wherein said surface elements are in a concentric annular arrangement.

4. The apparatus of claim 2 wherein said wave-emitting surface is elongated and rectangular.

5. The apparatus of claim 3 wherein outer ones of said concentrically arranged surface elements have longer radii of curvature than inner ones of said surface elements.

6. In an ultrasonic medical apparatus comprising an ultrasonic transducer having a wave-emitting surface, said transducer being adapted to have high-frequency electric power applied thereon, to thereby emit ultrasonic waves through said wave-emitting surface, and to focus said waves at a target position for a medical treatment, the improvement wherein said wave-emitting surface of said transducer is partitioned into a plurality of concave surface elements having different radii of curvature and different centers of concavity, said surface elements being in a concentric annular arrangement such that said ultrasonic waves emitted through said wave-emitted surface are focused at a plurality of specified positions, and outer ones of said concentrically arranged surface elements having a longer focal length than inner ones thereof.

7. An ultrasonic medical apparatus comprising:
   an ultrasonic transducer adapted to have high-frequency electric power applied thereon to thereby generate ultrasonic waves; and
   an acoustic lens having a wave-emitting surface, said acoustic lens being adapted to receive said ultrasonic waves generated by said transducer and to emit said ultrasonic waves through said wave-emitting surface so as to focus said emitted waves at a plurality of specified positions, said wave-emitting surface of said acoustic lens being partitioned into a plurality of concave surface elements having different radii of curvature and different centers of concavity.

8. The apparatus of claim 7 wherein said surface elements are in a concentric annular arrangement.

9. The apparatus of claim 8 wherein outer ones of said concentrically arranged surface elements have longer radii of curvature than inner ones of said surface elements.

10. The apparatus of claim 8 wherein outer ones of said concentric arranged surface elements have a longer focal length than inner ones thereof.

11. The apparatus of claim 7 wherein both said transducer and said wave-emitting surface are elongated and rectangular.

12. The apparatus of claim 11 wherein said transducer is planar and is attached to said acoustic lens by an adhesive.

* * * * *